(12) United States Patent
Schinazi et al.

(10) Patent No.: US 7,608,061 B2
(45) Date of Patent: *Oct. 27, 2009

(54) FLOW RESTRICTOR DEVICE FOR A MEDICAL APPARATUS

(76) Inventors: Robert G. Schinazi, 320 Pomelo Dr., Apt. 216, Vista, CA (US) 92081; Lauren E. de Rosset, 320 Pomelo Dr., Apt. 216, Vista, CA (US) 92081

( * ) Notice: Subject to any disclaimer, the term of this patent is extended or adjusted under 35 U.S.C. 154(b) by 764 days.

This patent is subject to a terminal disclaimer.

(21) Appl. No.: 10/909,752

(22) Filed: Aug. 2, 2004

(65) Prior Publication Data

US 2005/0197632 A1    Sep. 8, 2005

Related U.S. Application Data

(63) Continuation-in-part of application No. 10/791,682, filed on Mar. 2, 2004, now Pat. No. 7,364,571.

(51) Int. Cl.
*A61M 5/00* (2006.01)
(52) U.S. Cl. .................. 604/246; 604/537; 138/46
(58) Field of Classification Search ......... 604/246–247, 604/523, 251–262, 534–537, 890.1, 30, 118, 604/80, 81, 126, 186; 239/542; 138/40–46
See application file for complete search history.

(56) References Cited

U.S. PATENT DOCUMENTS

| | | | |
|---|---|---|---|
| 2,341,394 A | 2/1944 | Sloan | |
| 2,511,733 A | 6/1950 | Morrison | |
| 2,771,878 A | 11/1956 | Folland et al. | |
| 3,868,973 A * | 3/1975 | Bierman et al. | 138/43 |
| 3,815,636 A | 6/1975 | Menzel | |
| 4,022,384 A | 5/1977 | Hoyle et al. | |
| 4,200,119 A | 4/1980 | Cunningham | |
| 4,411,292 A | 10/1983 | Schiller | |
| 4,589,872 A * | 5/1986 | Bellin et al. | 604/246 |
| 4,639,019 A * | 1/1987 | Mittleman | 285/332 |

(Continued)

FOREIGN PATENT DOCUMENTS

EP    0 271 785    6/1988

(Continued)

OTHER PUBLICATIONS

PCT Search Report, Dec. 7, 2005.

(Continued)

*Primary Examiner*—Nicholas D Lucchesi
*Assistant Examiner*—Theodore J Stigell
(74) *Attorney, Agent, or Firm*—Dority & Manning, P.A.

(57) ABSTRACT

A medical apparatus flow restrictor includes a housing having an inlet housing member defining an inlet and a separate outlet housing member mated with said inlet housing member and defining an outlet from the flow restrictor. A fluid path is defined through the housing members between the inlet and outlet. Opposed flow restriction surfaces are defined between at a location along the fluid path such that fluid delivered to the inlet passes between the opposed flow restriction surfaces prior to flowing from the outlet. The opposed flow restriction surfaces have a relative degree of surface roughness and opposed surface area defined as a function of a desired flow rate of fluid through the restrictor.

30 Claims, 11 Drawing Sheets

U.S. PATENT DOCUMENTS

| | | | |
|---|---|---|---|
| 4,796,660 A * | 1/1989 | Bron | 137/504 |
| 4,878,649 A | 11/1989 | Baba et al. | |
| 5,032,264 A | 7/1991 | Geiger | |
| 5,156,680 A | 10/1992 | Orzechowski | |
| 5,163,920 A | 11/1992 | Olive | |
| 5,549,583 A * | 8/1996 | Sanford et al. | 604/535 |
| 5,609,303 A | 3/1997 | Cohen | |
| 6,497,685 B1 | 12/2002 | Dennehey et al. | |
| 6,550,956 B1 * | 4/2003 | Utracki et al. | 366/176.2 |
| 6,569,125 B2 | 5/2003 | Jepson et al. | |
| 6,569,128 B1 | 5/2003 | Christensen et al. | |
| 6,981,967 B2 * | 1/2006 | Massengale et al. | 604/174 |

FOREIGN PATENT DOCUMENTS

| | | |
|---|---|---|
| GB | 376 798 | 7/1932 |

OTHER PUBLICATIONS

European Search Report, April 6, 2009.

* cited by examiner

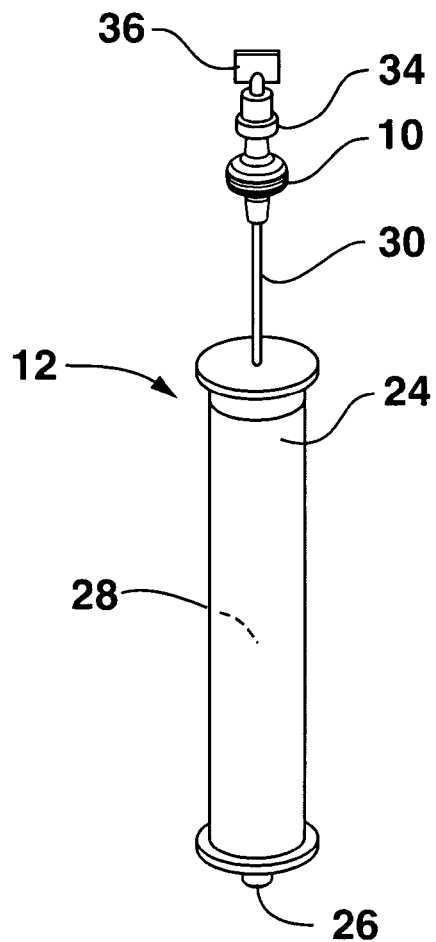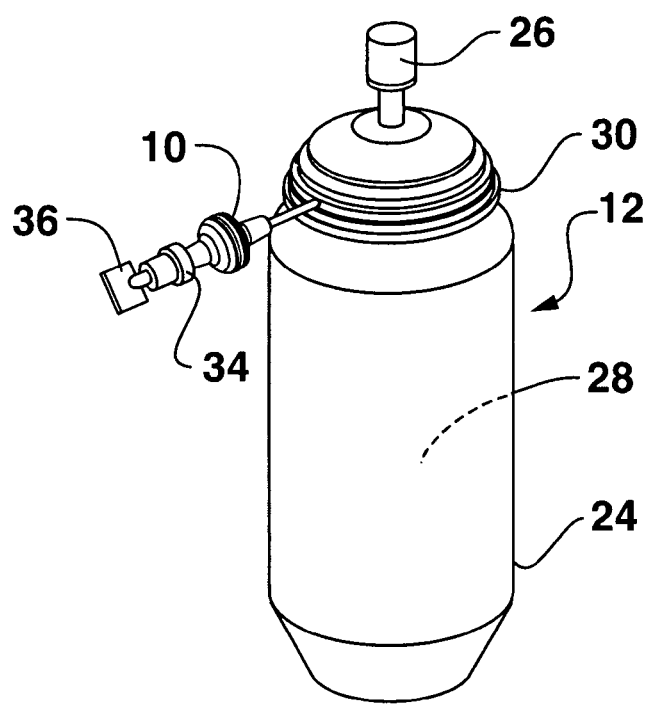
FIG. 1B  FIG. 1C

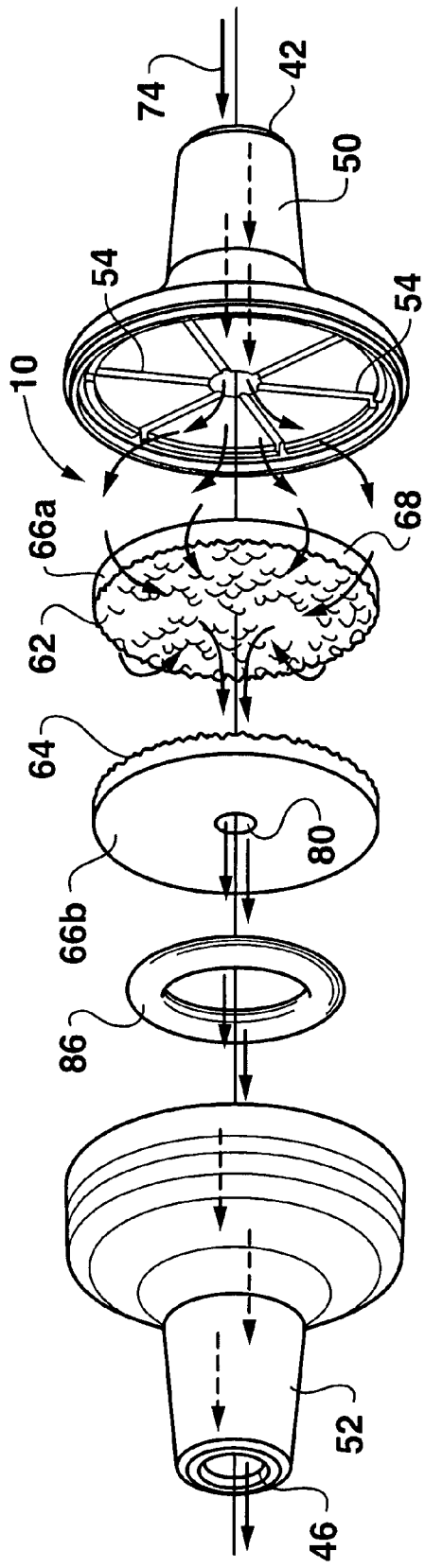
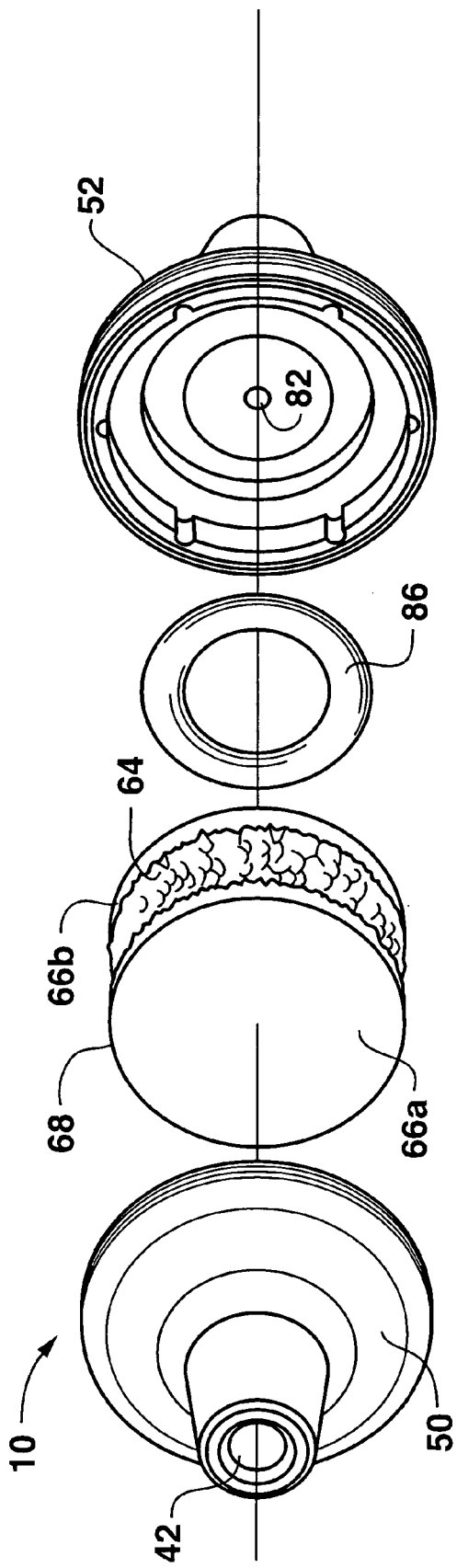
FIG. 4A
FIG. 4B

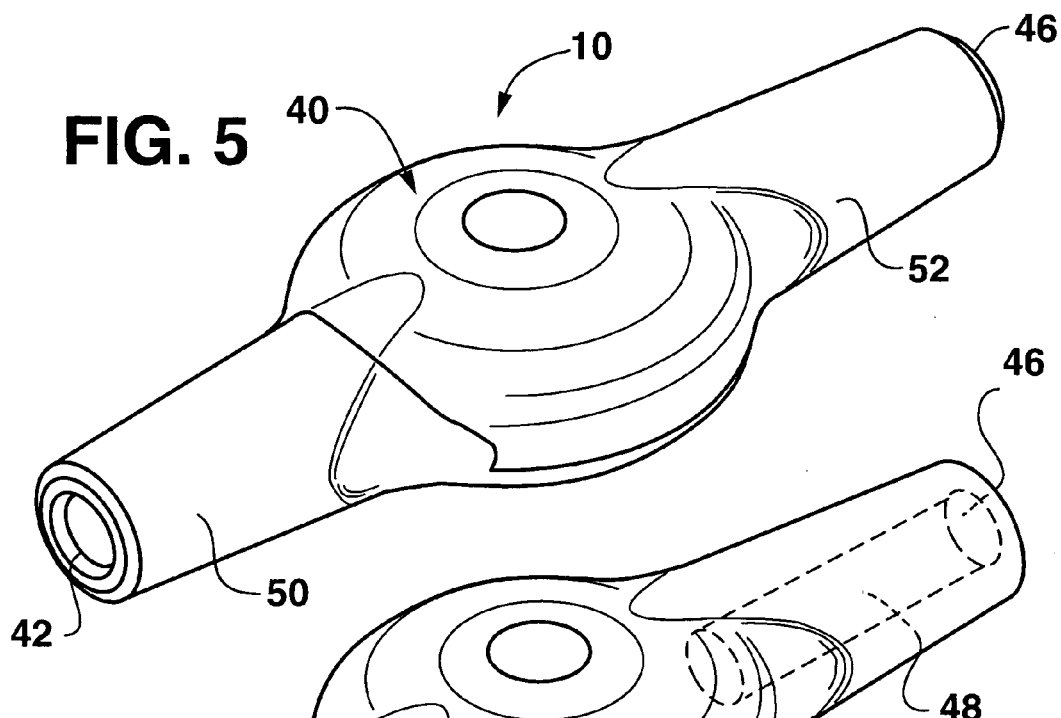
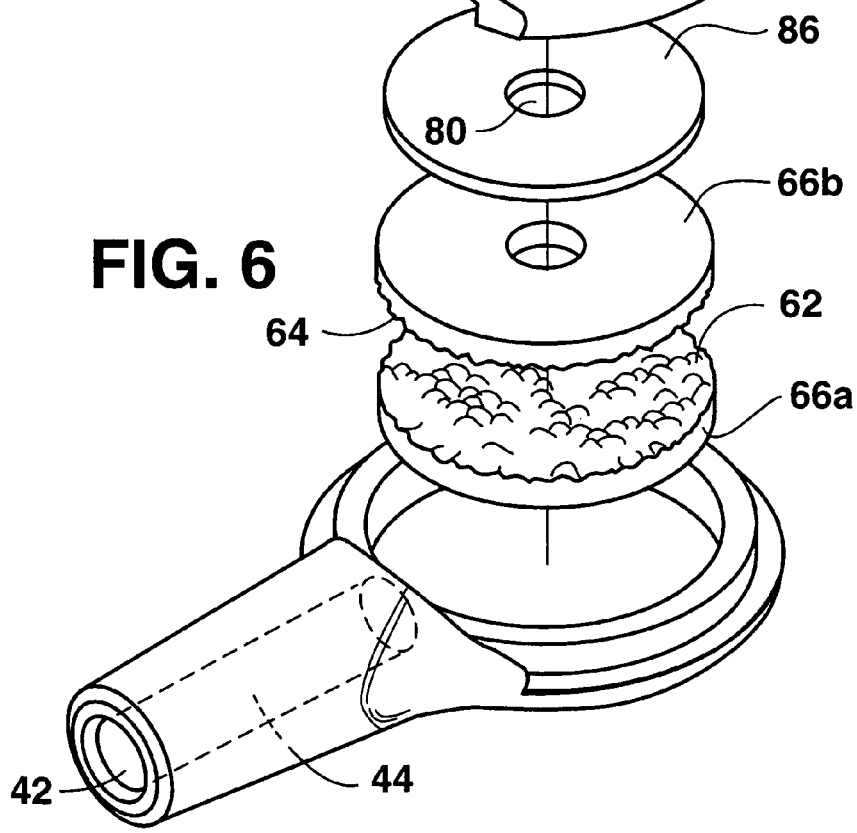

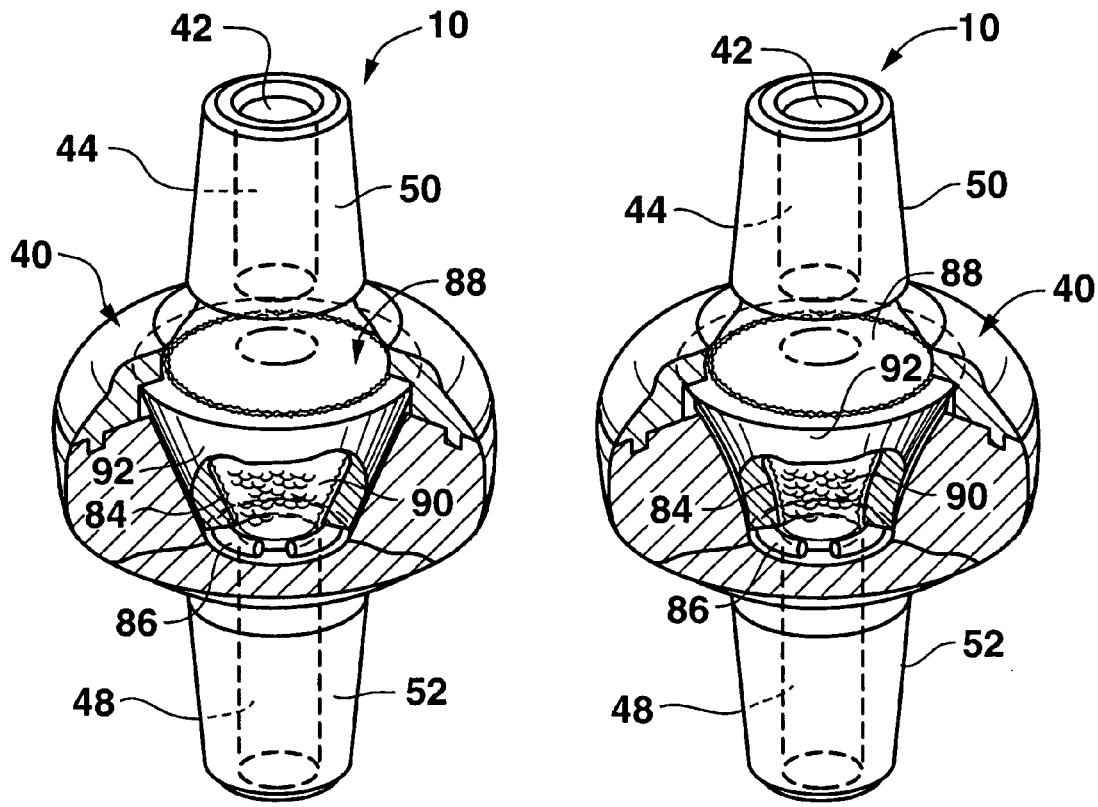
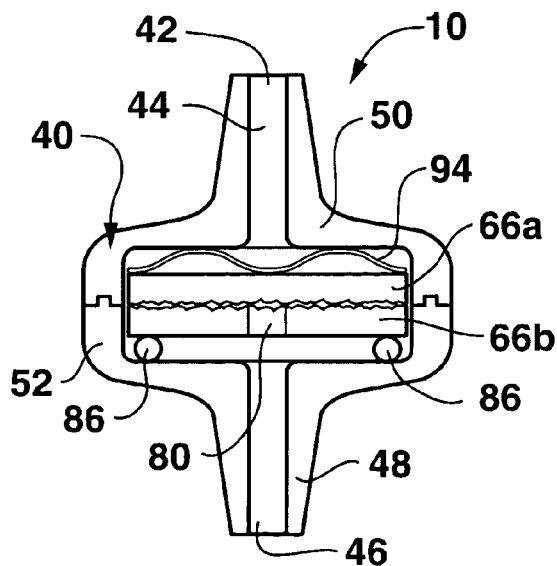
FIG. 9
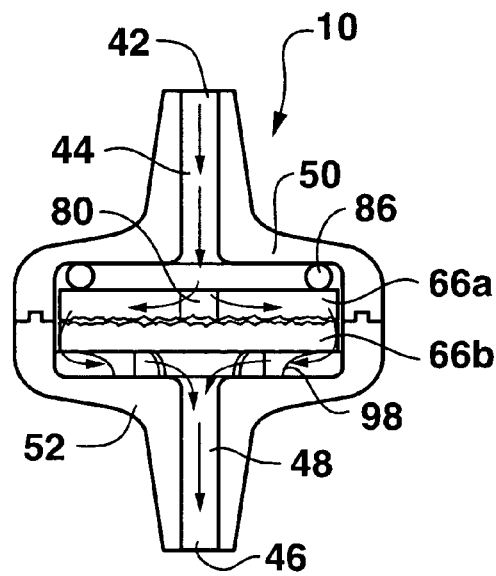
FIG. 10

FLOW RESTRICTOR DEVICE FOR A MEDICAL APPARATUS

RELATED APPLICATION

The present application claims priority as a Continuation-in-Part application to U.S. application Ser. No. 10/791,682 filed on Mar. 2, 2004, now U.S. Pat. No. 7,364,571.

FIELD OF THE INVENTION

The present invention relates generally to the field of flow restriction devices, and more specifically to a flow restrictor that is particularly well suited for regulating the flow of fluids in various medical devices and systems.

BACKGROUND OF THE INVENTION

There are various applications of flow restriction devices in the medical arts for closely regulating the flow of a fluid. One common use of such devices is with an infusion pump system wherein fluid medicine or other fluids are delivered to an injection site on the patient from an infusion pump. Embodiments are known wherein the flow restrictor is contained within the pump body. For example, U.S. Pat. No. 4,386,929 describes a short capillary tube contained within the pump housing for regulating the flow of dispensed medication. It is also known to include a flow restrictor downstream of the infusion pump, for example as with the delivery tube system described in U.S. Pat. No. 4,741,733.

U.S. Pat. No. 6,569,128 describes a catheter flow restriction system wherein a capillary-like restriction tube is contained within a catheter tube. The flow rate through the system is adjusted by trimming the length of the restriction tube and concentric catheter tube. The catheter can then be attached to an infusion device by a suitable connector, such as a Touhy-Borst connector.

Conventional flow restriction devices are, however, not without certain drawbacks, particularly the capillary tube restrictors. For example, such tube-type devices are relatively difficult and expensive to manufacture. Also, as requirements in the medical field tend towards decreased flow rates, it has become increasingly difficult to manufacture the tubes to achieve a specified flow rate due simply to machining tolerances and material limitations. For example, the smaller (in diameter) the tubes become, the more prone they become to particulate clogging.

A need thus exists in the medical field for a more reliable yet inexpensive flow restrictor that may be used in various systems, such as infusions systems and like devices.

SUMMARY OF THE INVENTION

Objects and advantages of the invention will be set forth in part in the following description, or may be obvious from the description, or may be learned through practice of the invention.

In accordance with the invention, a flow restrictor device is provided that is relatively inexpensive to manufacture and assemble, yet will reliably maintain a precisely regulated flow rate. The device is not prone to clogging, and is easily incorporated into any conventional medical infusion or other type of fluid delivery system. In this regard, it should be appreciated that although the inventive restrictor has particular usefulness in an infusion delivery system, the invention is not limited to this particular application. The inventive restrictor may be used in any system wherein it is desired to restrict or regulate the flow of a fluid, and all such uses are within the scope and spirit of the invention.

The term "fluid" is used herein to refer to a gas, liquid, or combination of a gas and liquid.

The flow restrictor according to the invention includes a housing having an inlet and an outlet, and a fluid path defined through the housing between the inlet and outlet. The inlet and outlet are configured to be connected in-line, for example with tubing or the like, in a medical apparatus, such as an infusion system. The inlet and outlet may be releasably connected to the medical apparatus tubing, for example with a simple press fit, clamp, or fitting, or permanently attached by, for example, by way of an adhesive, ultrasonic bond, a weld, and so forth.

At least one pair of opposed restriction devices are seated within the housing between the inlet and outlet. The restriction devices have opposing surfaces placed in contact against each other and are disposed in the flow path such that fluid delivered to the inlet must pass between the opposing surfaces prior to flowing from the outlet. Any one or combination of seals, such as O-rings, gaskets, or the like, may be used within the housing to establish the desired flow path through the devices. A resilient member, such as a spring, wave spring, or similar device may be used to bias the restriction devices together. Alternatively, the seal may be resilient and also function to bias the restriction devices together.

The opposing surfaces of the restriction devices have a relative degree of surface roughness and opposed surface area that are predetermined as a function of a desired flow rate of fluid through the restrictor. Thus, the restrictive flow path between the opposed surfaces of the restriction devices has a metering or restrictive effect on the rate of flow through the device, as described in greater detail below.

The restriction devices may take on various shapes and be formed from any number of suitable materials, such as glass, ceramic, steel, and so forth. For example, in one particular embodiment, the restriction devices are opposed flat planar members disposed within the housing such that fluid from the inlet flows radially between the opposing surfaces. In one particular embodiment, fluid from the inlet is directed to the outer circumference of the restriction devices and flows radially inward between the opposing surfaces. The bottom (downstream) member has an orifice defined therethrough that defines an exit path for the fluid from between the planar members. The orifice is aligned with, or otherwise in fluid communication with, the housing outlet.

In an alternate embodiment, the upstream restriction device (e.g., an upstream flat planar member) may have an opening or orifice and the flow path within the housing is established such that fluid flows through this orifice and then migrates radially outward between the opposing surfaces prior to flowing to the outlet.

The flat planar member restriction devices may take on various shapes, sizes, thicknesses, etc. In one particular embodiment, the members are circular discs stamped or otherwise formed from a desired material. Such devices may be desired from the standpoint of ease of manufacture and assembly.

It should be appreciated that it is not necessary that each of the opposing surfaces is purposefully roughened as compared to the other. A desired relative degree of surface roughness along the restrictive flow path may be achieved by treating only one of the surfaces. The other surface may be untreated and relatively smooth. Alternately, the surfaces may have an inherent degree of surface roughness such that neither surface need be treated.

In an alternate embodiment, the restriction devices may be defined by a conical male member that mates within a complimentary shaped recess such that the opposing surfaces are defined by the conical wall of the male member and the recess wall. The conical member may have straight sides (i.e., constant slope) or curved sides. This embodiment may be desired in that a larger surface area between the opposing surfaces of the restriction devices may be achieved, thus permitting a greater degree of metering or fluid restriction.

In yet another embodiment, the restriction devices may be defined by a ball member seated within a ball seat such that the opposing surfaces are defined by a circumferential portion of the ball member and the ball seat. One or both of these surfaces may be roughened.

The restriction devices may be formed of a hard, non-compressible material, such as a medical grade stainless steel, so that fluid flow between the opposing surfaces is substantially constant regardless of a compressive pressure applied to restriction devices from fluid pressure or assembly of the housing components. In an alternate embodiment, the restriction devices may be formed of a compressible material, such as a medical grade polymer material, so that fluid flow between the opposing surfaces may be changed or adjusted by varying a compressive pressure applied to the restriction devices, for example by way of housing components that may be threadedly engaged.

In a particular embodiment, the housing comprises separate halves, with the restriction devices being placed within the halves prior to joining the halves to form the complete housing. The halves may be separable after being joined for access to the restriction devices. For example, the halves may be threaded onto each other, or otherwise releasably engaged. Alternatively, the halves may be permanently joined, for example by way of an adhesive, weld, and so forth.

The restriction devices may be variously oriented within the housing relative to the inlet and outlet. For example, in one embodiment, the devices are disposed such that a plane between the opposing surfaces is generally perpendicular to an axis of the inlet and outlet. In an alternate embodiment, the restriction devices are disposed such that the plane between the opposing surfaces is generally parallel to an axis of the inlet and outlet.

In an alternate preferred configuration of a flow restrictor device in accordance with the invention, the opposed flow restriction surfaces may be defined directly on opposed surfaces of the housing members. For example, a first flow restriction surface may be formed as an integral surface on an inlet housing member, and a second flow restriction surface may be formed as an integral surface of an outlet housing member. Upon mating the inlet and outlet housing members, the respective flow restriction surfaces are opposed and the fluid path through the restrictor flows between the opposed flow restriction surfaces, with the fluid flow being a function of a compressive force between the housing members.

In a particular embodiment, a forward portion of the inlet housing member is received within a recess defined in the outlet housing member. The first opposed flow restriction surface is formed directly on the forward portion of the inlet housing member, and the second opposed flow restriction surface is formed directly in the recess of the outlet housing member. Alternatively, the recess may be formed in the inlet housing member, and the portion received in the recess may be formed on the outlet housing member.

The recess and mating portion may have various shapes and configurations. For example, in one particular embodiment, the forward portion of the inlet housing member comprises a tapered conical configuration, and the recess defined in the outlet housing member has a corresponding tapered conical configuration. In an alternate embodiment, the recess may have a semi-spherical configuration, or a cylindrical configuration with a flat planar flow restriction surface, and the portion received in the recess has a corresponding shape.

The inlet and outlet housing members may be formed of various suitable materials. In a particularly desirable embodiment, the members are molded from a polymer material such as a medical grade plastic. At least one of the flow restrictions surfaces is compressible to a degree such that fluid flow between the opposed flow restriction surfaces is varied by varying a compressive pressure applied to the inlet and outlet housing members. In this regard, the portion of the housing member defining the flow restriction surface may be formed of a compressible plastic. Alternatively, the housing members may be formed entirely of the same material, for example molded from a plastic material. Alternately, the housing member or members may be made of a relatively hard non-compressible material with only the flow restriction surfaces being made of a compressible material added to the harder material as a layer, cap, etc.

To ensure that fluid flow through the restrictor is directed between the opposed flow restriction surfaces, a seal such as an O-ring, gasket, and so forth, may be disposed at a suitable location between the inlet and outlet housing members. The inlet and outlet housing members may be mated together by various conventional methods. For example, the members may be glued, bonded, welded, and so forth. The members may be permanently fixed together, or releasably attached.

The respective surface roughness of the opposed flow restriction surfaces may be an inherent result of the process used to manufacture the housing member, such as a molding process, or may be defined in a subsequent step by any one or combination of a controlled grinding, lapping, tumbling, sandblasting, or etching process. In a particularly desirable embodiment, the inlet and outlet housing members are molded components, and the surface roughness of the opposed flow restriction surfaces are molded surfaces. The opposed flow restriction surfaces may have the same relative roughness, or different degrees of roughness.

As with the other embodiments of the flow restrictor, the inlet and outlets of the housing members may be connectable to tubing in fluid delivery system such that the restrictor is placeable in-line within such a system.

The housing members may be permanently fixed together, for example by use of an adhesive, weld, or any other conventional attaching method depending on the particular type of material used to manufacture the housing members. In a particular embodiment, the housing members are molded plastic components, and an adhesive such as a UV cured adhesive may be used to fix the members together to ensure the desired flow rate is a permanent characteristic of the restrictor.

Alternately, the housing members may be separable. For example, there may be uses of the restrictor in systems wherein flow rates may need to be adjusted or varied without removing the restrictor from the system. Depending on the fluid conducted, certain systems may require the components to be made of relatively expensive corrosion resistant materials wherein it is not economically feasible to discard the restrictors or carry a large inventory of restrictors for various flow rates. It may thus be desired to vary the flow rate through the restrictor by varying the compressive force between the housing members. A threaded connection between the housing members, or other suitable adjustable connection, may be used for this purpose.

The predetermined compressive force used to achieve the desired flow rate may be determined in various ways. For example, the flow rate may be calculated from know variables and geometries related to the housing members, such as surface area and roughness of the opposed flow restriction surfaces, compressibility of the housing member materials, pressure of fluid through the system, and so forth. This calculated compressive force may then be used to assemble the components together.

In an alternative embodiment, the compressive force may be empirically determined in a carefully controlled simulation. For example, the components may be assembled in a testing apparatus that measures compressive force and flow rate through the restrictor as the compressive force is applied. Thus, flow rate as a function of compressive force may be readily determined for housing members of a given geometry, material, etc. The testing apparatus may be implemented with computer controls and analysis for precisely applying, varying, and measuring compressive pressure, as well as flow rate through the restrictor.

It should be readily apparent to those skilled in the art that such a testing apparatus may be configured in numerous ways, and with various commercially available equipment, or machinery configured specifically for the desired purpose.

The invention also encompasses any manner of medical fluid delivery system that incorporates one or more of the unique fluid restriction devices as described herein.

The invention will be described in greater detail below by reference to particular embodiments shown in the referenced figures.

BRIEF DESCRIPTION OF THE FIGURES

FIG. 1B is a perspective view of a conventional portable medical infusion system incorporating a flow restrictor according to the invention.

FIG. 1C is a perspective view of yet another conventional medical infusion system incorporating a flow restrictor according to the invention.

FIG. 4A is an in-line component view of an embodiment of the flow restrictor particularly illustrating the fluid flow path from the inlet to the outlet.

FIG. 4B is an in-line component view of the embodiment of FIG. 4A taken from the opposite direction.

FIG. 5 is a perspective view of an alternate embodiment of a flow restrictor according to the invention.

FIG. 6 is a component view of the embodiment of FIG. 5.

FIG. 7 is a perspective and partial cut-away view of an alternative embodiment of a flow restrictor according to the invention utilizing conical restriction devices.

FIG. 8 is a perspective and partial cut-away view of an alternative embodiment of a flow restrictor according to the invention utilizing conical restriction devices having radially curved side walls.

FIG. 9 is a cross-sectional diagrammatic view of an alternate embodiment of a flow restrictor incorporating a biasing element with the housing.

FIG. 10 is a cross-sectional diagrammatic view of an embodiment of a flow restrictor having a flow path such that fluid flows radially outward between the opposed surfaces of the restriction devices.

DETAILED DESCRIPTION

Reference will now be made in detail to examples of the invention, one or more embodiments of which are illustrated in the figures. Each example is provided by way of explanation of the invention, and not meant as a limitation of the invention. For example, features illustrated or described as part of one embodiment may be used with another embodiment to yield still a further embodiment. It is intended that these and other modifications and variations be included within the scope and spirit of the invention.

Figure 1A:
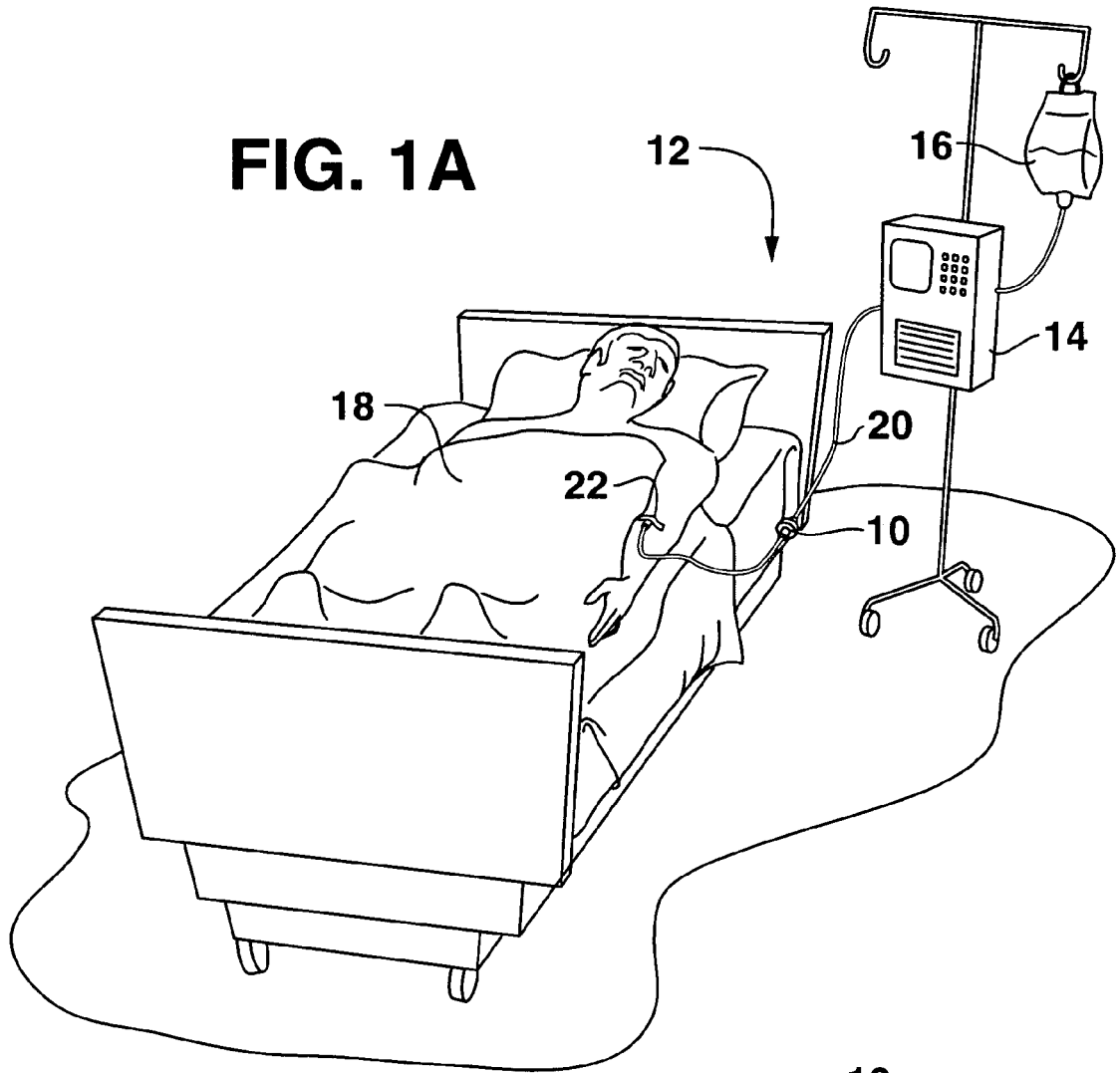
FIG. 1A is a perspective view of a conventional infusion pump system incorporating a flow restrictor according to the invention.

FIG. 1A illustrates an embodiment of a medical system, generally 12, that may utilize a flow restrictor 10 according to the invention. The medical system 12 is illustrated as a conventional infusion system wherein an infusion pump 14 is supplied with a fluid, such as a medicine, by a solution container 16 that is supported at a given height above the pump 14. Tubing 20 supplies the fluid from the pump 14 to an intravenous (IV) site 22 on a patient 18. Such infusion systems and pumps 14 are well known by those skilled in the medical art. Such systems are supplied, for example, by Braun Medical, Inc. of Bethlehem, Pa., and Baxter Healthcare Corporation of Round Lake, Ill. The flow restrictor 10 is illustrated as connected in-line in the tubing 20 between the pump 14 and the patient 18. It should also be appreciated that the restrictor 10 may be incorporated within the housing of the pump 14.

FIGS. 1B and 1C illustrate portable infusion systems that are generally worn or carried by a patient. Such devices are commercially available, for example, from Baxter Healthcare Corporation. FIG. 1B illustrates a small-volume system wherein a housing 24 defines an internal reservoir 28. A flexible membrane, such as an elastomeric balloon or the like, is contained within the reservoir 28 and provides fluid pressure. A fill port and associated cap 26 are provided for filling the reservoir 28. Delivery tubing 30 connects the housing 24 to a delivery end connector 34, such as a conventional luer connector. A cap 36 is provided for the connector 34. A flow restrictor 10 in accordance with the invention is provided in-line in the tubing 30 between the connector 34 and the housing 24. The connector 10 may be removably connected in the tubing 30, or permanently attached in the tubing 30, as described in greater detail below.

The infusion device of FIG. 1C is similar to that of FIG. 1B, but includes a larger housing 24 and internal reservoir 28. The reservoir 28 also includes an elastomeric "balloon" type of member for holding the fluid medication under sufficient pressure for delivery to the patient.

Although described with reference to infusion-type systems, it should be readily appreciated that the flow restrictor 10 according to the invention may be used in any medical system wherein it is desired to deliver a metered amount of a fluid to a patient from a pressurized source. For example, the restrictor 10 according to the invention can be utilized for continuous or intermittent delivery of fluids through clinically acceptable routes of administration, such as intravenous (IV), intra-arterial (IA), subcutaneous, epidural, or irrigation of fluid spaces applications.

Figure 2:
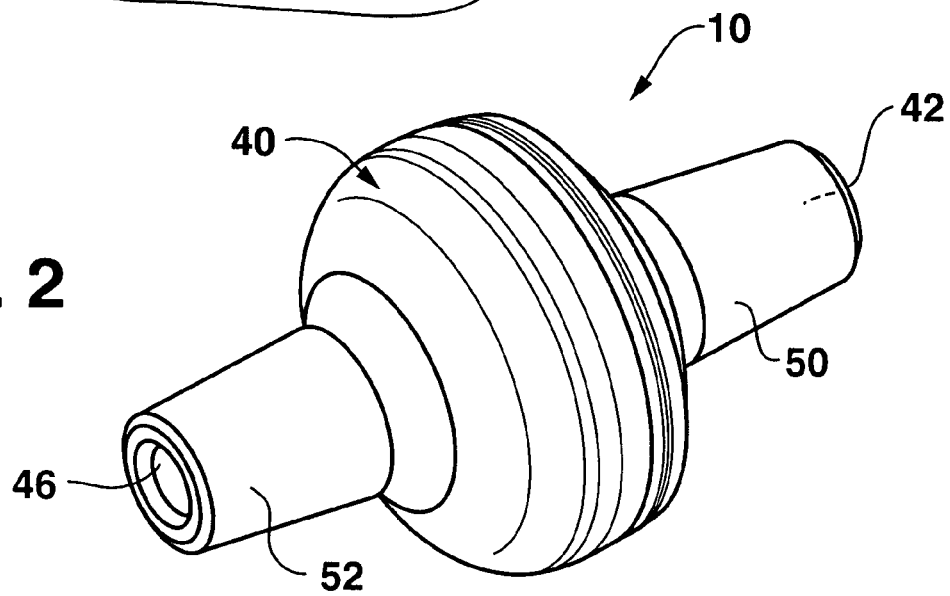
FIG. 2 is a perspective view of an embodiment of a flow restrictor according to the invention.

FIG. 2 illustrates an embodiment of the flow restrictor 10 in accordance with the invention. The restrictor 10 includes a housing 40 that may take on generally any desired shape or design. The housing 40, in one particular embodiment, is defined by separate halves or elements 50, 52, as described in greater detail below. The flow restrictor 10 includes an inlet 42 through which fluid is introduced into the device 10, and an outlet 46 from which fluid is conducted after flowing through the device 10.

Referring to FIGS. 3A through 3C, 4A, and 4B, the flow restrictor 10 of FIG. 2 is illustrated in greater detail. Housing 40 includes a first half 50 and a second half 52. The first half 50 defines the inlet 42 and an inlet passage 44. Similarly, the second half 52 defines an outlet passage 48 and the outlet 46. The halves 50, 52, may be configured to be releasably attached to medical tubing, for example by way of a clamp, or a simple friction or press fit of the tubing over the elongated ends of the respective halves 50, 52. Alternately, the tubing may be permanently attached to the respective halves 50, 52, by an adhesive, weld, or any other suitable permanent attachment means.

Figure 3A:
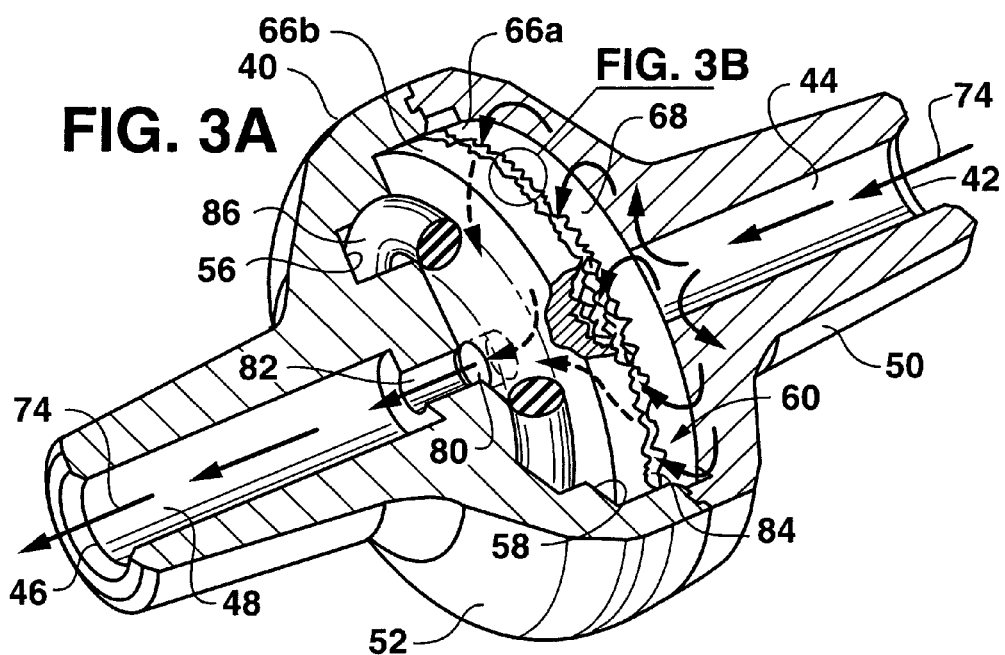
FIG. 3A is a cross-sectional view of the flow restrictor of FIG. 2, particularly illustrating the flow path for a fluid through the device.
Figure 3B:
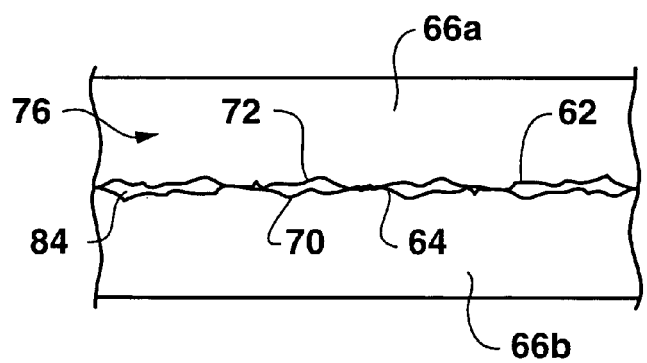
FIG. 3B is an enlarged view of the section of the circumference of the flow restriction devices indicated in FIG. 3A.
Figure 3C:
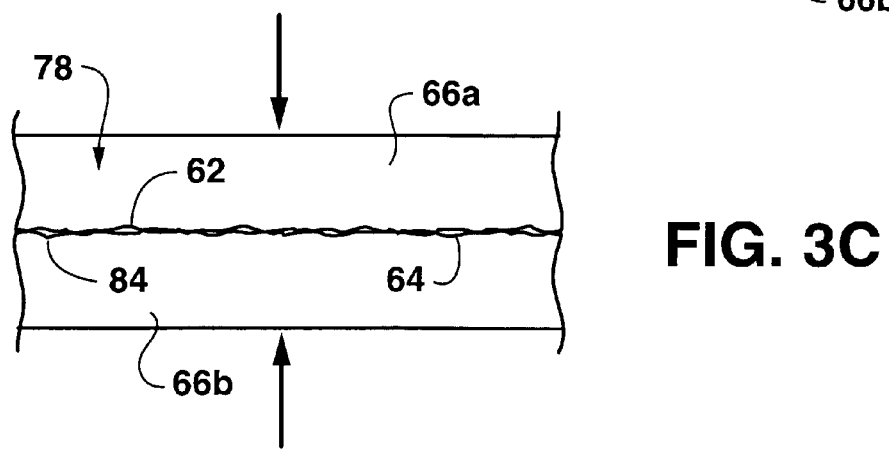
FIG. 3C is a side view of an embodiment of compressible flow restriction devices.

At least one pair of opposed restriction devices 60 are seated within the housing 40 between the inlet 42 and the outlet 46. The restriction devices 60 may take on various forms, so long as they define opposed surfaces placed in contact against each other such that a restrictive flow field 84 is defined between the opposed surface that intermittently contact at a plurality of locations between the opposed surfaces. For example, in the embodiment illustrated in the figures, the restriction devices 60 are defined by generally flat planar members 66a and 66b disposed against each other. The planar members may take on any shape, and in the figures are depicted as circular disks contained in the housing 40 by way of disk seats 58. Referring particularly to FIGS. 3A and 3B, it can be seen that at least one of the disks 66a or 66b, includes a generally "rough" surface such that when the opposing surfaces 62 and 64 are placed against each other, the restrictive fluid flow field 84 is defined between the surfaces. In the illustrated embodiment, each of the disks includes a roughened surface, as particularly seen in FIG. 3B. In this manner, there exists void spaces or valleys 72 and protrusions 70 that define a completely random restrictive flow field 84. It should be appreciated that the degree of surface roughness between the opposing surfaces 62, 64, is grossly exaggerated in the figures for purposes of illustration only. It may very well be that, for many embodiments, the surface roughness is not discernible by the unaided eye.

By carefully controlling the degree of surface roughness of the opposed surfaces 62, 64, the rate of fluid flow between the matrix of valleys 72 and protrusions 70 along the field 84 may be controlled, and a relatively precise metering mechanism is defined. For a specific fluid pressure, a desired fluid flow rate can be achieved by carefully defining the particular parameters of surface roughness of each of the surfaces 62, 64, the surface area of contact between the surfaces 62, 64, and the pressure applied to the surfaces 62, 64. Taking these factors into consideration, the restriction devices 66a and 66b may be designed for a particular flow rate based on prediction algorithms. Alternatively, the dimensions and surface roughness of the devices 66a, 66b, may be empirically determined through routine experimentation.

The cylindrical disk-type restriction devices 66a, 66b, may be desired in that they are relatively inexpensive and easy to fabricate. For example, the components may be punched, stamped, turned, and so forth. Also, the desired degree of surface roughness of the disks 66a, 66b, may be achieved with conventional processes such as etching, sandblasting, lapping, grinding, tumbling, and so forth.

In the embodiment illustrated in FIGS. 3A and 3B, the restriction devices 66a, 66b, are formed from a relatively incompressible, hard material, such as stainless steel, glass, ceramic, and so forth. In this manner, the restrictive flow path 84 is predominantly unchanged or unaltered by the degree of compression of the devices against each other. Alternatively, it may be desired that the devices 66a, and 66b, are formed from a compressible material, such as a relatively soft poly material. In this manner, the restrictive field 84 may be made more or less restrictive depending upon the degree of compression of the components 66a, 66b, against each other, as is diagrammatically illustrated in FIG. 3C. The "soft" disks 66a, 66b, may be used in an embodiment wherein the housing halves 50, 52, are relatively adjustable relative to each other, for example as in a threaded engagement between the two halves. With this configuration, different flow rates may be achieved with a single restrictor 10, or the restrictor may be adjusted or fine-tuned for achieving a very accurate flow rate.

FIGS. 3A and 4A illustrate the flow path 74 of a fluid through one embodiment of the restrictor 10. In this particular embodiment, the fluid moves under pressure through the inlet 42 and inlet passage 44 and is directed to the perimeter or circumference 68 of the restriction devices 66a, 66b, by way of relief channels 54 or other suitable structure defined in the housing half 50. A sealing device 86, such as a conventional O-ring, gasket, or any other suitable elastomeric sealing device, is disposed in a seat 56 in the housing second half 52, as particularly seen in FIG. 3A. This seal 86 prevents the fluid from bypassing the restrictive field 84. Referring particularly to FIG. 3A, it can be seen that the fluid migrates from the circumference of the restriction devices 66a, 66b radially inward at a rate that is defined as a function of the surface roughness and surface area of the opposed surfaces 62, 64, of the restriction devices, as discussed above. The fluid migrates to an orifice 80 defined in the downstream restriction device 66b. The orifice 80 is in fluid communication with the outlet passage 48, for example by way of an orifice passage 82.

It should be appreciated that any number of configurations of internal structure, sealing devices, and so forth, may be utilized within a housing 40 to ensure that fluid is directed through the restrictive field 84 of opposed restriction devices 66a, 66b to disburse the fluid from the outlet 46 at a desired flow rate. It may be desired to incorporate the sealing element in the housing, for example by way of a two-shot injection molding process wherein the second shot is an elastomer. Alternatively, a sealing element may be provided on one or both of the disks 66a, 66b (or other type of restriction devices). For example, the disks 66a, 66b may be stamped from a composite metal/rubber sheet wherein the metal component defines an opposing surface of the restriction device, and the rubber component defines the seal. In still an alternative embodiment, the seal need not be elastomeric. For example, the seal may be defined by an epoxy, glue, or ultrasonic bond between the disk and a housing member.

Thus far, the restrictor 10 according to the invention has been described with opposed roughened surfaces 62, 64.

However, it should be appreciated that the invention also includes the configuration wherein only one of the surfaces 62, 64, is roughened. In other words, the restrictive flow field 84 may be achieved by opposed surfaces wherein one of the surfaces is relatively smooth or polished with respect to the other surface. Alternatively, for ease of manufacturing, assembly, and so forth, it may be desired that all of the components are essentially the same and axis-symmetric. For example, if both sides of the restriction disk 66a, 66b are treated (rough), then assembly is facilitated by eliminating a particular surface to surface orientation. This design is optimized for pick-and-place automated assembly.

It should also be appreciated that, for varying flow rates, several restrictive devices may be stacked within a common housing.

The halves of the housing 40 may be releasably attached to each other after insertion of the sealing device 86 and restriction devices 66a, 66b, or permanently attached to each other. For example, the halves, 50, 52, may be threadedly engaged such that the device 10 may be subsequently taken apart for replacement of the restriction devices 66a, 66b. In an alternative embodiment, the halves 50, 52 may be permanently adhered to each other with an adhesive, ultrasonic bonding, welding, or any other conventional attaching means.

It should also be appreciated that the restriction devices 66a, 66b, may be variously oriented within the housing 40. For example, in the embodiment illustrated in FIGS. 3A, 4A, and 4B, the devices 66a and 66b are oriented such that a plane between the opposing surfaces 62, 64, is generally perpendicular to the axis of the inlet and outlet of the housing 40. FIGS. 5 and 6 illustrate an alternative embodiment wherein the restriction devices 66a, 66b, and seal 86 (gasket) are oriented within the housing 40 such that the plane between the restriction devices is generally parallel to the axis of the inlet and outlet of the housing 40. Regardless of the orientation of the restriction devices 66a, 66b, the operation of the device is essentially as described above with reference to the embodiment of FIGS. 3A and 4A, and 4B.

It should also be appreciated that the restriction devices 60 may take on various shapes and configurations. For example, in the embodiments of FIGS. 7 and 8, conical restriction devices 88 are provided. A conical or truncated male member 90 having a rough outer surface is seated within a correspondingly shaped recess of an opposite member 92. The restrictive flow path is thus defined between the conical walls of the members 90 and 92, wherein at least one of these opposed surfaces defines a roughened surface. In the embodiment of FIG. 7, the conical opposed surfaces are relatively straight in that they have a constant slope. In the embodiment of FIG. 8, the opposed conical surfaces are curved, or have a radial component along at least a portion thereof. The embodiments of FIGS. 7 and 8 provide for an increased surface area between the opposed surfaces defining the restrictive flow field 84, as compared to the flat disk devices 66a, 66b, of the prior embodiments.

Figure 11:
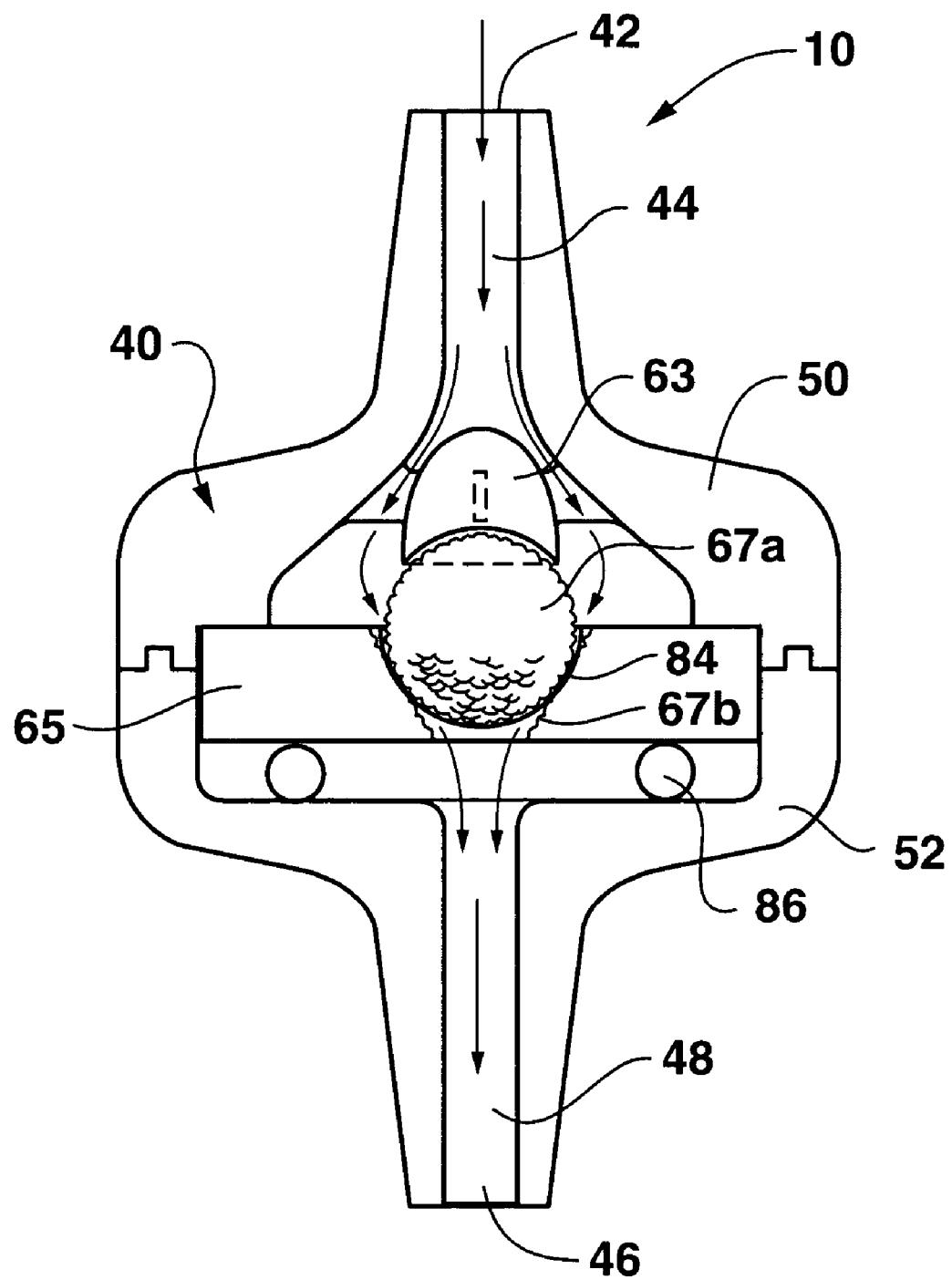
FIG. 11 is a cross-sectional diagrammatic view of an embodiment of a flow restrictor wherein the restriction devices include a ball seated within a ball seat.

FIG. 11 illustrates an embodiment of a flow restrictor 10 wherein the restriction devices are defined by a ball member 67a and a planar member 65 having a ball seat 67b defined therein. The restrictive fluid flow path 84 is defined between the circumferential portion of the ball member 67a and surface of the ball seat 67b. Either one or both of the ball surface or ball seat may be roughened. A flow distributor 63 may be incorporated within the housing as an integrally formed or separate component. The distributor 63 may take on any shape to direct fluid from the inlet passage 44 to the restrictive fluid flow path 84 and may also serve to positively engage and contain the ball 67a within the ball seat 67b. This embodiment may be desired from the standpoint of cost and ease of manufacture.

It should be appreciated that various configurations of restrictive devices may be derived empirically or otherwise by those skilled in the art to define a restrictive flow field between opposed surfaces in accordance with the principles of the present invention.

FIG. 9 illustrates an embodiment of a restrictor 10 incorporating a resilient biasing element within the housing 40. The biasing element may be in the form of a wave spring 94 as illustrated in the FIG. 9, or may be any other conventional biasing element such as a spring, and so forth. The biasing element serves to ensure that the restriction devices 66a, 66b are biased together so that the opposing surfaces properly define the desired restrictive flow path. It should also be appreciated that the sealing element 86 in the embodiments of FIG. 3a and FIG. 11, for example, may be formed of an elastomeric material and may also serve the function of biasing the restriction devices together.

FIG. 10 is an embodiment of a restrictor 10 wherein the fluid flows in a radially outward direction along the restrictive flow path between the restriction devices 66a, 66b. An orifice 80 is defined generally at the center of the upstream restriction device 66a. The sealing device (ring) 86 is disposed concentric about the orifice 80 such that fluid entering from inlet passage 44 is caused to flow through the orifice 80 to the restrictive flow path defined by the opposing surfaces of the restriction devices 66a, 66b. The fluid then flows radially outward along the flow path, as indicated by the arrows in FIG. 10, and around the periphery of the downstream restriction device 66b where it is directed to the outlet passage 48. Ridges 98, or any other suitable support structure, are provided within the housing to support the restriction device 66b and define a flow path for the fluid to the outlet passage 48.

FIGS. 12 through 15 illustrate various other embodiments of restrictors according to the invention wherein opposing flow restriction surfaces are defined directly on mated housing members. For example, a first flow restriction surface may be formed as an integral surface on an inlet housing member, and a second flow restriction surface may be formed as an integral surface of an outlet housing member. Upon mating the inlet and outlet housing members, the respective flow restriction surfaces are opposed and the fluid path through the restrictor flows between the opposed flow restriction surfaces, with the fluid flow being a function of a compressive force between the housing members. It should be appreciated that much of the discussion set forth above with respect to FIGS. 1 through 11 applies equally to the embodiments of FIGS. 12 through 15 and need not be repeated.

Figure 12:
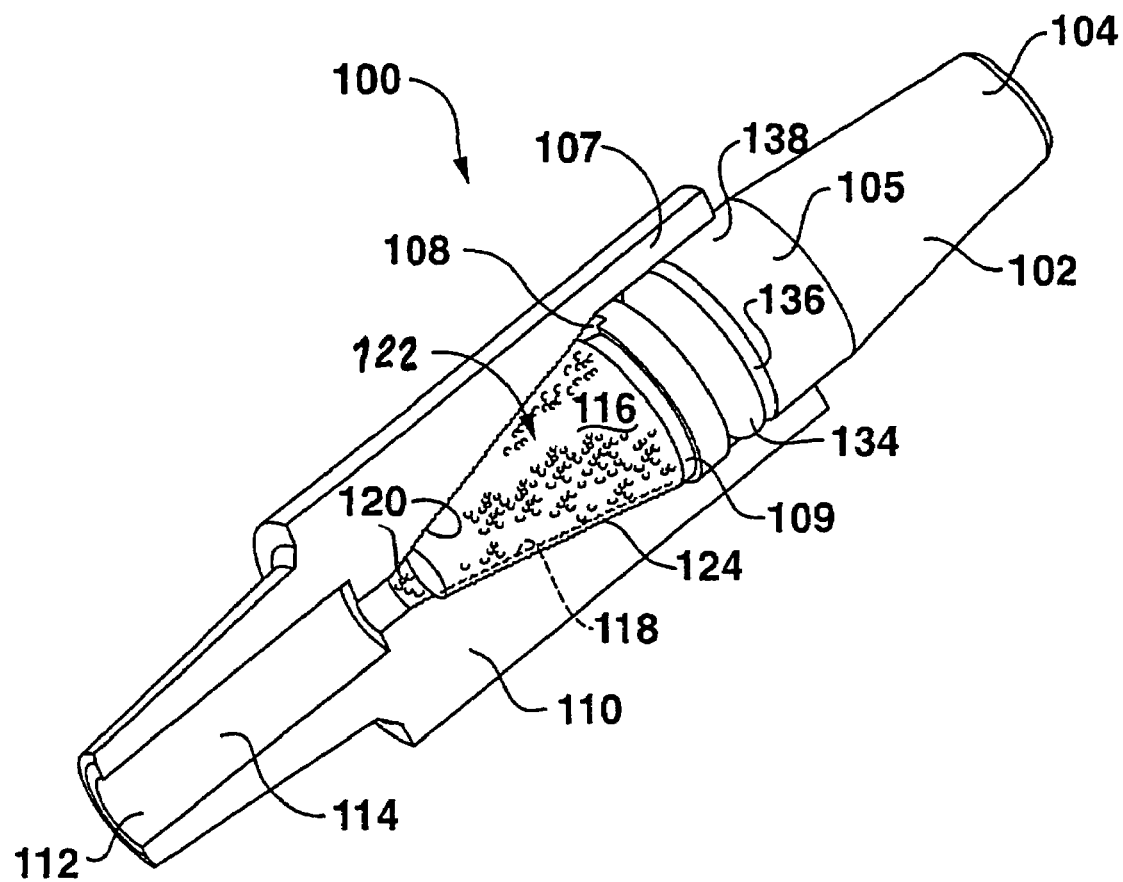
FIG. 12 is a cross-sectional view of an alternate preferred embodiment of a flow restrictor according to the invention.
Figure 13:
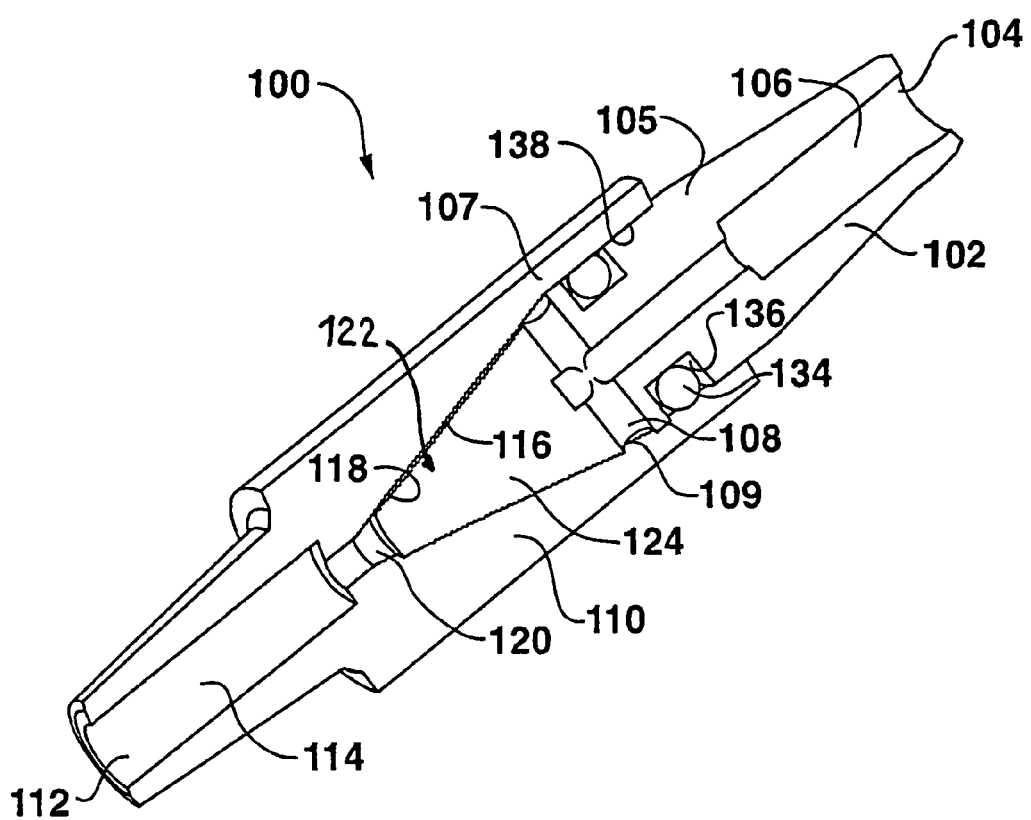
FIG. 13 is a more detailed cross-sectional view of the embodiment of the restrictor of FIG. 12.

Referring to FIGS. 12 and 13 in particular, a flow restrictor 100 includes an inlet housing member 102 and an outlet housing member 110 shown in their mated configuration. The housing members 102, 110 may take on any desired shape and appearance so long as a fluid flow path is defined between an inlet and an outlet of the restrictor 100. In the illustrated embodiment, the inlet housing member 102 is a generally elongated member defining an inlet opening 104, a passage 106, and a forward portion 105. Similarly, the outlet housing member 110 is an elongated member defining an outlet 112, a passage 114, and a receiving portion 107 that mates with the forward portion 105 of the inlet housing member 102.

Opposed flow restriction surfaces are formed on respective surfaces of the inlet and outlet housing members 102, 110 such that a portion of the fluid flow path through the restrictor is defined between the flow restriction surfaces. For example, in the embodiment of FIGS. 12 and 13, a first flow restriction surface 116 is provided as the surface of a protrusion 122 of the inlet housing member 102, and an opposed second flow restriction surface 118 is provided on the surface of a recess 120 defined in the outlet housing member 110. The recess 120 has a shape corresponding to the shape of the protrusion 122. It should be appreciated that the protrusion 122 may be provided on the outlet housing member 110, and the recess 120 defined in the inlet housing member 102.

Referring to FIG. 13, fluid flowing through the restrictor 100 enters the inlet 104, travels internally along the passage 106, and migrates radially outward along the radial passage 108. The fluid then enters a circumferentially extending relief channel 109. From the channel 109, the fluid must migrate along the tortuous flow path defined between the opposed flow restriction surfaces 116, 118, before entering the outlet passage 114 and exiting the restrictor 100 through the outlet 112. Compression of the opposed flow restriction surfaces 116, 118 is the controlling factor in setting a desired flow rate through the restrictor 100.

The flow restriction surfaces 116, 118 may be defined as an integral surface of their respective housing members. For example, the surfaces 116, 118 may be directly molded with the housing members with a predetermined surface roughness. The desired surface roughness may simply be an inherent characteristic of the material and process used to form the housing members 102, 110. Alternatively, the desired surface roughness may be provided in a subsequent fabrication step, such as any one or combination of a controlled grinding, lapping, tumbling, sandblasting, or etching process. The opposed flow restriction surfaces 116, 118 may have the same relative roughness, or different degrees of roughness.

It is also within the scope of the invention to form the housing members 102, 110 of different materials, wherein the flow restriction surfaces 116, 118 are defined in a material that is different from the remaining portion of the housing member. For example, the housing members 102, 110 may be formed from a composite material wherein the portion defining the flow restriction surface is a plastic material, and the remainder of the housing member is metal. Alternatively, the flow restriction surfaces 116, 118 may be defined on members that are subsequently attached to separately formed components to define a complete housing member. Any number of configurations and combinations of materials are possible.

The recess 120 and mating protrusion 122 may have various shapes and configurations. For example, in the embodiment of FIGS. 12 and 13, the protrusion 122 is a tapered conical member 122, and the recess 120 is a correspondingly shaped tapered recess. The tapered configuration may be desired in that, if the angle of taper is selected correctly, the housing members 102, 110 become essentially self-locking, which decreases reliance on a subsequent bonding step. The taper angle should be essentially at or slightly below the self-clinching angle for the given material used to form the housing members 102, 110. For example, for polycarbonate materials, the self-clinching angle is approximately 15 degrees (30 degree included angle). Additionally, the taper converts the majority of applied stress into "hoop" stress, which is advantageous from structural and stability considerations.

As the relative degree of compression of the opposed flow restriction surfaces 116, 118 establishes the desired flow rate, the flow restriction surfaces 116, 118 are formed in materials that have at least some degree of relative compression when the housing members 102, 110 are pressed together. The surfaces 116, 118 may be formed of the same materials and thus have the same degree of compressibility, or be formed of different materials and have different degrees of compressibility. In a preferred embodiment, the housing members 102, 110 and their respective flow restriction surfaces 116, 118 are formed of the same polymer material, such as a medical grade polycarbonate. It should be readily understood that the particular material selected is a function of the environment in which the restrictor 100 is intended. For example, in medical chemotherapy applications, plastic materials that are resistant to chemotherapy drugs are desired.

Referring again to FIGS. 12 and 13, a seal 134 is provided between the inlet and outlet housing members 102, 110. This seal 134 may be any conventional sealing device, such as an O-ring, gasket, mechanical seal, and so forth. The seal 134 is desirably an inert material that will not react with the fluid flowing through the restrictor 100. In the illustrated embodiment, the seal 134 is disposed in a recess 136 defined around a portion of the inlet housing member 102 that mates within the receiving portion 107 in the outlet housing member 110. In this position, the seal 134 prevents fluid from flowing out from between the mated housing members. The seal 134 also aids in sealing the housing members 102, 110 during a telescoping assembly process wherein flow rate is fine tuned by adjusting the degree of compression of the housing components 102, 110.

It may also be desired to permanently fix the housing members 102, 110 together to "set" the degree of compression of the opposed flow restriction surfaces 116, 118. This may be accomplished in various conventional ways, including adhesives, welds, and so forth. In a particular embodiment, a UV-cured adhesive may be applied to a mating section of the housing members, such as along the longitudinally extending region 138 between the forward portion 105 of the inlet housing member 102 and the receiving section 107 of the outlet housing member 110. The UV adhesive allows for relative adjustment between the housing members until such time as the mated members are exposed to UV light to cure the adhesive.

In an alternative embodiment, it may be desired to non-permanently set the relative position of the housing members 102, 110 so that the members can be subsequently adjusted, or even separated. For example, a threaded connection, press-fit or compression connection may be used to allow for subsequent relative movement between the housing members.

Figure 14:
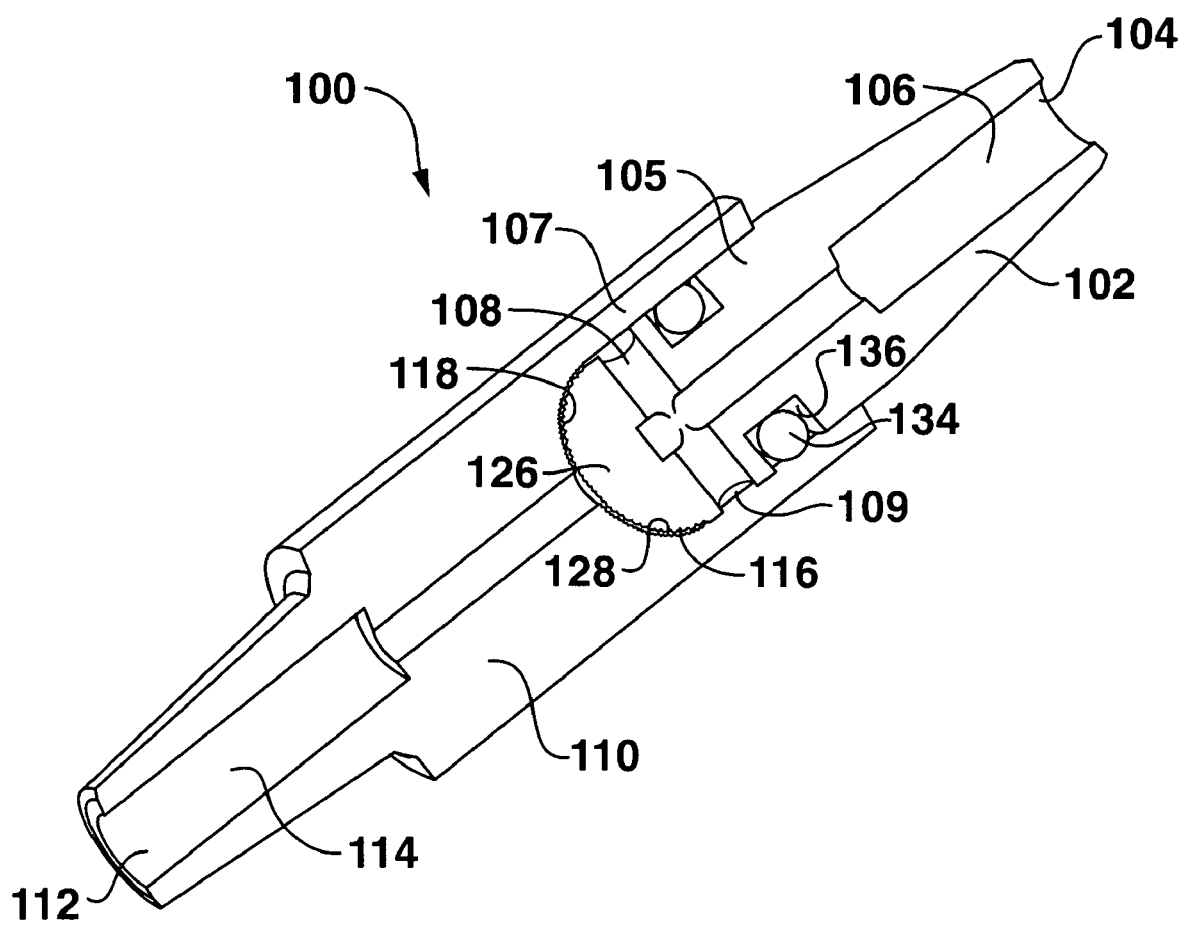
FIG. 14 is a cross-sectional view of an additional embodiment of a flow restrictor according to the invention.

The flow restrictor 100 illustrated in FIG. 14 is similar to that of FIGS. 12-13 with the exception of the shape of the opposed flow restriction surfaces 116, 118. A semispherical protrusion 126 at the forward end of the inlet housing member 102 defines the first flow restriction surface 116, and a correspondingly shaped semispherical recess 128 defined in the outlet housing member 110 defines the second flow restriction surface 118.

Figure 15:
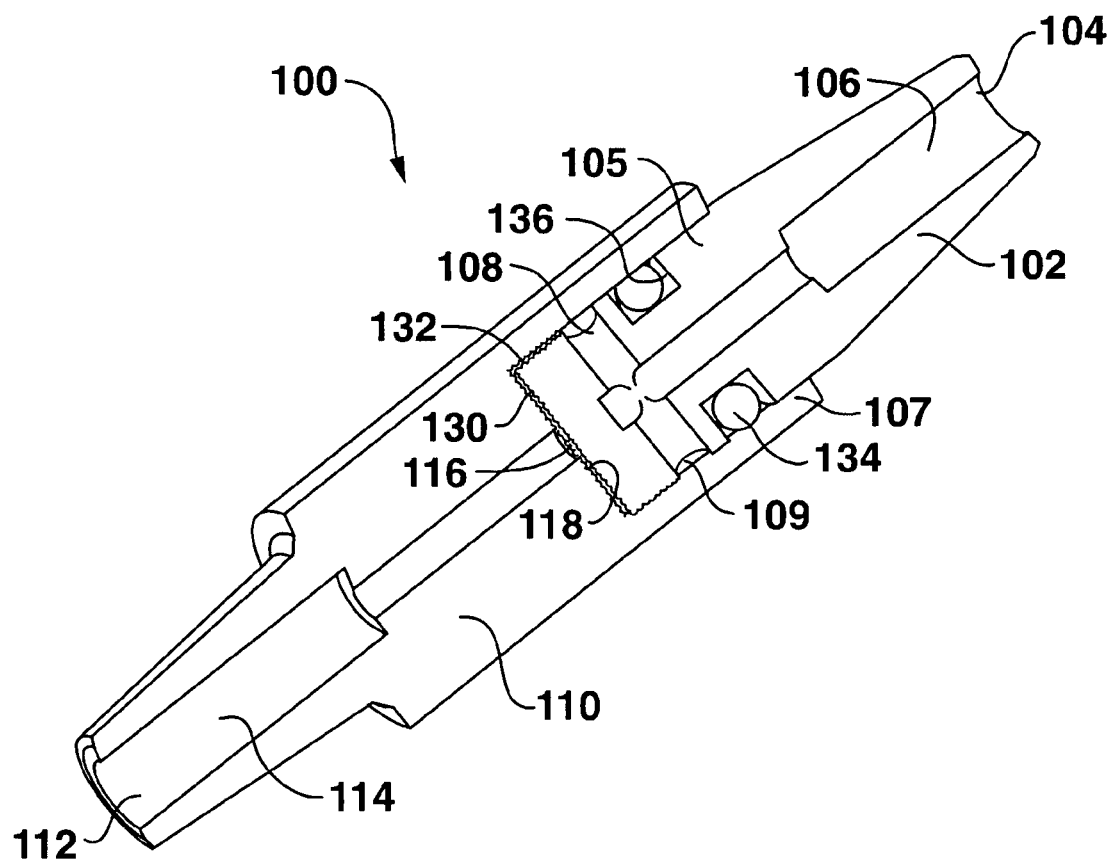
FIG. 15 is a cross-sectional view of still another embodiment of a flow restrictor according to the invention.

In the embodiment of a flow restrictor 100 shown in FIG. 15, the opposed flow restriction surfaces 116, 118 are defined as planar surfaces oriented in a plane generally perpendicular to a longitudinal axis of the restrictor 110. The first flow restriction surface 116 is defined on the planar front end 130 of the inlet housing member 102, and the second flow restriction surface 118 is defined on the planar surface of the cylindrical recess 132.

It should be appreciated that any number of various shapes and configurations of components may be used to define the opposed flow restriction surfaces 116, 118.

As with the other embodiments of the flow restrictor described above, the inlet 104 and outlet 112 of the housing members may be connectable to tubing in a fluid delivery system, particularly a medical system, such that the restrictor is placeable in-line within such a system.

The predetermined compressive force used to achieve the desired flow rate may be determined in various ways. For example, the flow rate may be calculated from know variables and geometries related to the housing members 102, 110, such as surface area and roughness of the opposed flow restriction surfaces, compressibility of the housing member materials, pressure of fluid through the system, and so forth. This calculated compressive force may then be used to assemble the components together.

Alternatively, the compressive force may be empirically determined in a carefully controlled simulation. For example, the components may be assembled in a testing apparatus that measures compressive force and flow rate through the restrictor as the compressive force is applied. Thus, flow rate as a function of compressive force may be readily determined for housing members of a given geometry, material, etc. It is well within the level of those skilled in the arts to configure various suitable machines that may be used for determining the desired compressive force between the housing members.

It should be appreciated by those skilled in the art that modifications and variations may be made to the embodiments described above without departing from the scope and spirit of the invention. It is intended that the invention include these and other modifications as come within the scope and spirit of the appended claims and their equivalents.

What is claimed is:

1. A medical apparatus flow restrictor, comprising:
   an inlet housing member defining an inlet to said flow restrictor, and a separate outlet housing member mated with said inlet housing member and defining an outlet from said flow restrictor;
   a fluid path defined through said inlet and outlet housing members between said inlet and said outlet;
   flow restriction surfaces defined on opposing surfaces of said inlet and outlet housing members, said flow restriction surfaces contacting each other intermittently at a plurality of locations along said fluid path such that fluid delivered to said inlet passes between said opposed flow restriction surfaces of said inlet and outlet housing members prior to flowing from said outlet; and
   wherein said opposed flow restriction surfaces have a random surface roughness and opposed surface area defined as a function of a desired flow rate of fluid through said restrictor, said opposed flow restriction surfaces defining a flow field of random surface contours to restrict and regulate fluid flow through said restrictor.

2. The restrictor as in claim 1, wherein a first of said opposed flow restriction surfaces is formed as an integral surface on said inlet housing member, and a second of said opposed flow restriction surfaces in formed as an integral surface of said outlet housing member.

3. The restrictor as in claim 2, wherein one of said first or second opposed flow restriction surfaces is formed in a recess, and the other of said respective second or first flow restriction surface is formed on a protrusion that extends into said recess.

4. The restrictor as in claim 3, wherein a forward portion of said inlet housing member defines said protrusion, and said recess is defined in said outlet housing member.

5. The restrictor as in claim 3, wherein said protrusion comprises a generally semi-spherical configuration, and said recess comprises a corresponding semi-spherical configuration.

6. The restrictor as in claim 3, wherein said protrusion comprises a generally flat planar surface, and said recess comprises a corresponding flat planar surface.

7. The restrictor as in claim 3, wherein said inlet housing member is pressed into mating configuration with said outlet housing member such that said opposed flow restriction surfaces are pressed together to a predetermined degree sufficient for providing a desired fluid flow through said restrictor.

8. The restrictor as in claim 1, further comprising a seal disposed between said inlet and outlet housing members to ensure that fluid flow through said restrictor is directed between said opposed flow restriction surfaces.

9. The restrictor as in claim 1, wherein said inlet and outlet housing members are permanently and non-separably joined.

10. The restrictor as in claim 1, wherein a plane between said opposed flow restriction surfaces is generally perpendicular to an axis of said inlet and said outlet.

11. The restrictor as in claim 1, wherein a plane between said opposed flow restriction surfaces is a generally curved plane with respect to an axis of said inlet and said outlet.

12. The restrictor as in claim 1, wherein said inlet and said outlet are connectable to tubing in fluid delivery system such that said restrictor is placeable in-line within said system.

13. The restrictor as in claim 1, wherein said surface roughness of at least one of said opposed flow restriction surfaces is defined in any one or combination of a controlled grinding, lapping, tumbling, sandblasting, or etching process.

14. The restrictor as in claim 1, wherein said inlet and outlet housing members are molded components, and said surface roughness of said opposed flow restriction surfaces are molded surfaces.

15. A medical apparatus flow restrictor, comprising:
   an inlet housing member defining an inlet to said flow restrictor and further defining a forward portion, and a separate outlet housing member mated with said inlet housing member and defining an outlet from said flow restrictor and further defining a recess;
   a fluid path defined through said inlet and outlet housing members between said inlet and said outlet;
   flow restriction surfaces defined on opposing surfaces of said inlet and outlet housing members, said flow restriction surfaces contacting each other intermittently at a plurality of locations along said fluid path such that fluid delivered to said inlet passes between said opposed flow restriction surfaces of said inlet and outlet housing members prior to flowing from said outlet; wherein said opposed flow restriction surfaces have a random surface roughness and opposed surface area defined as a function of a desired flow rate of fluid through said restrictor, said opposed flow restriction surfaces defining a flow field of random surface contours to restrict and regulate fluid flow through said restrictor; and
   wherein said forward portion of said inlet housing member comprises a tapered conical configuration, and said recess of said outlet housing member comprises a corresponding tapered conical configuration.

16. A medical apparatus flow restrictor, comprising:
   an inlet housing member defining an inlet to said flow restrictor, and a separate outlet housing member mated with said inlet housing member and defining an outlet from said flow restrictor;
   a fluid path defined through said inlet and outlet housing members between said inlet and said outlet;
   flow restriction surfaces defined on opposing contacting surfaces of said inlet and outlet housing members at a location along said fluid path such that fluid delivered to said inlet passes between said opposed flow restriction surfaces of said inlet and outlet housing members prior to flowing from said outlet;
   wherein said opposed flow restriction surfaces have a random surface roughness and opposed surface area defined as a function of a desired flow rate of fluid through said restrictor, said opposed flow restriction surfaces defining a flow field of random surface contours to restrict and regulate fluid flow through said restrictor;

wherein said inlet housing member is pressed into mating configuration with said outlet housing member such that said opposed flow restriction surfaces are pressed together to a predetermined degree sufficient for providing a desired fluid flow through said restrictor; and wherein at least one of said opposed flow restriction surfaces is formed of a compressible material such that fluid flow between said opposed flow restriction surfaces is varied by varying a compressive pressure applied to said inlet and outlet housing members.

17. The restrictor as in claim 16, wherein each of said opposed flow restriction surfaces is formed of a compressible material such that fluid flow between said opposed flow restriction surfaces is varied by varying a compressive pressure applied to said inlet and outlet housing members.

18. The restrictor as in claim 17, wherein said compressible material is a medical grade polymer material.

19. The restrictor as in claim 18, wherein said inlet and outlet housing members are formed entirely of said polymer material.

20. A medical apparatus flow restrictor, comprising:
    an inlet housing member defining an inlet to said flow restrictor, and a separate outlet housing member mated with said inlet housing member and defining an outlet from said flow restrictor;
    a fluid path defined through said inlet and outlet housing members between said inlet and said outlet;
    flow restriction surfaces defined on opposing contacting surfaces of said inlet and outlet housing members at a location along said fluid path such that fluid delivered to said inlet passes between said opposed flow restriction surfaces of said inlet and outlet housing members prior to flowing from said outlet;
    wherein said opposed flow restriction surfaces have a random surface roughness and opposed surface area defined as a function of a desired flow rate of fluid through said restrictor, said opposed flow restriction surfaces defining a flow field of random surface contours to restrict and regulate fluid flow through said restrictor; and
    wherein a plane between said opposed flow restriction surfaces is a generally conical plane with respect to an axis of said inlet and said outlet.

21. A medical apparatus flow restrictor, comprising:
    an inlet housing member defining an inlet to said flow restrictor, and a separate outlet housing member mated with said inlet housing member and defining an outlet from said flow restrictor;
    a fluid path defined through said inlet and outlet housing members between said inlet and said outlet;
    flow restriction surfaces defined on opposing surfaces of said inlet and outlet housing members, said flow restriction surfaces contacting each other intermittently at a plurality of locations along said fluid path such that fluid delivered to said inlet passes between said opposed flow restriction surfaces of said inlet and outlet housing members prior to flowing from said outlet;
    wherein said opposed flow restriction surfaces have a random surface roughness and opposed surface area defined as a function of a desired flow rate of fluid through said restrictor, said opposed flow restriction surfaces defining a flow field of random surface contours to restrict and regulate fluid flow through said restrictor; and
    wherein one of said opposed flow restriction surfaces comprises a rougher surface as compared to said other flow restriction surface.

22. A medical fluid delivery system configured to deliver a fluid from a source to a patient at a regulated flow rate, said system comprising delivery tubing and a flow restrictor placed in-line in said tubing, said flow restrictor further comprising:
    an inlet housing member defining an inlet to said flow restrictor, and a separate outlet housing member mated with said inlet housing member and defining an outlet from said flow restrictor;
    a fluid path defined through said inlet and outlet housing members between said inlet and said outlet;
    flow restriction surfaces defined on opposing surfaces of said inlet and outlet housing members, said flow restriction surfaces contacting each other intermittently at a plurality of locations along said fluid path such that fluid delivered to said inlet passes between said opposed flow restriction surfaces of said inlet and outlet housing members prior to flowing from said outlet;
    wherein said opposed flow restriction surfaces have a random surface roughness and opposed surface area defined as a function of a desired flow rate of fluid through said restrictor, said opposed flow restriction surfaces defining a flow field of random surface contours to restrict and regulate fluid flow through said restrictor.

23. The fluid delivery system as in claim 22, wherein said flow restrictor is disconnectable from said tubing.

24. The fluid delivery system as in claim 22, wherein a first of said opposed flow restriction surfaces is formed as an integral surface on said inlet housing member, and a second of said opposed flow restriction surfaces is formed as an integral surface of said outlet housing member.

25. The fluid delivery system as in claim 24, wherein a forward portion of said inlet housing member is received within a recess defined in said outlet housing member, said first opposed flow restriction surface formed on said forward portion of said inlet housing member, and said second opposed flow restriction surface formed in said recess of said outlet housing member.

26. A medical fluid delivery system configured to deliver a fluid from a source to a patient at a regulated flow rate, said system comprising delivery tubing and a flow restrictor placed in-line in said tubing, said flow restrictor further comprising:
    an inlet housing member defining an inlet to said flow restrictor, and a separate outlet housing member mated with said inlet housing member and defining an outlet from said flow restrictor;
    a fluid path defined through said inlet and outlet housing members between said inlet and said outlet;
    flow restriction surfaces defined on opposing contacting surfaces of said inlet and outlet housing members at a location along said fluid path such that fluid delivered to said inlet passes between said opposed flow restriction surfaces of said inlet and outlet housing members prior to flowing from said outlet;
    wherein said opposed flow restriction surfaces have a random surface roughness and opposed surface area defined as a function of a desired flow rate of fluid through said restrictor, said opposed flow restriction surfaces defining a flow field of random surface contours to restrict and regulate fluid flow through said restrictor;
    wherein a first of said opposed flow restriction surfaces is formed as an integral surface on said inlet housing member, and a second of said opposed flow restriction surfaces is formed as an integral surface of said outlet housing member;

wherein a forward portion of said inlet housing member is received within a recess defined in said outlet housing member, said first opposed flow restriction surface formed on said forward portion of said inlet housing member, and said second opposed flow restriction surface formed in said recess of said outlet housing member; and wherein said forward portion of said inlet housing member comprises a tapered conical configuration, and said recess of said outlet housing member comprises a corresponding tapered conical configuration.

27. The fluid delivery system as in claim 26, wherein said inlet housing member is pressed into mating configuration with said outlet housing member such that said opposed flow restriction surfaces are pressed together to a predetermined degree sufficient for providing a desired fluid flow through said restrictor.

28. A medical fluid delivery system configured to deliver a fluid from a source to a patient at a regulated flow rate, said system comprising delivery tubing and a flow restrictor placed in-line in said tubing, said flow restrictor further comprising:

an inlet housing member defining an inlet to said flow restrictor, and a separate outlet housing member mated with said inlet housing member and defining an outlet from said flow restrictor;

a fluid path defined through said inlet and outlet housing members between said inlet and said outlet;

flow restriction surfaces defined on opposing contacting surfaces of said inlet and outlet housing members at a location along said fluid path such that fluid delivered to said inlet passes between said opposed flow restriction surfaces of said inlet and outlet housing members prior to flowing from said outlet;

wherein said opposed flow restriction surfaces have a random surface roughness and opposed surface area defined as a function of a desired flow rate of fluid through said restrictor, said opposed flow restriction surfaces defining a flow field of random surface contours to restrict and regulate fluid flow through said restrictor; and wherein each of said opposed flow restriction surfaces is formed of a compressible material such that fluid flow between said opposed flow restriction surfaces is varied by varying a compressive pressure applied to said inlet and outlet housing members.

29. The fluid delivery system as in claim 28, wherein said compressible material is a medical grade polymer material.

30. The fluid delivery system as in claim 29, wherein said inlet and outlet housing members are formed entirely of said polymer material.

* * * * *